US005804729A

United States Patent [19]
Andersen

[11] Patent Number: 5,804,729
[45] Date of Patent: Sep. 8, 1998

[54] APPARATUS AND ASSOCIATED METHOD FOR MEASURING DIFFERENCES IN DELAY MEASUREMENTS

[75] Inventor: Jorgen W. Andersen, Orlando, Fla.

[73] Assignee: Sawtek Inc., Orlando, Fla.

[21] Appl. No.: 563,398

[22] Filed: Nov. 28, 1995

[51] Int. Cl.[6] .................................................. G01N 29/00
[52] U.S. Cl. ............................................. 73/609; 73/617
[58] Field of Search .............................. 73/24.01, 24.06, 73/24.04, 19.03, 703, 609, 610, 611, 617; 364/506, 508, 576

[56] References Cited

U.S. PATENT DOCUMENTS

| 3,596,182 | 7/1971 | Menard | 325/67 |
|---|---|---|---|
| 3,698,508 | 10/1972 | Landrum | 73/594 |
| 3,906,213 | 9/1975 | Meriaux et al. | 235/181 |
| 3,914,987 | 10/1975 | Bickel | 73/609 |
| 4,014,208 | 3/1977 | Moore | 73/610 |
| 4,167,879 | 9/1979 | Pedersen | 73/610 |
| 4,173,007 | 10/1979 | McKeighen | 73/609 |
| 4,312,228 | 1/1982 | Wohltjen | 73/597 |
| 4,315,228 | 2/1982 | Moore | 333/193 |
| 4,512,198 | 4/1985 | Sinha et al. | 73/703 |
| 4,534,223 | 8/1985 | Sinha et al | 73/703 |
| 4,895,017 | 1/1990 | Pyke et al. | 73/23 |
| 4,995,019 | 2/1991 | Begin | 368/117 |
| 5,012,668 | 5/1991 | Haworth | 73/24.06 |
| 5,076,094 | 12/1991 | Frye et al. | 73/19.03 |
| 5,117,146 | 5/1992 | Martin et al. | 310/313 |
| 5,129,262 | 7/1992 | White et al. | 73/599 |
| 5,235,235 | 8/1993 | Martin et al. | 310/313 |
| 5,283,037 | 2/1994 | Baer et al. | 422/82.01 |
| 5,289,715 | 3/1994 | Staples et al. | 73/24.01 |
| 5,323,636 | 6/1994 | McGowan et al. | 73/24.01 |
| 5,325,704 | 7/1994 | Mariani et al. | 73/24.06 |
| 5,384,541 | 1/1995 | Chu et al. | 324/617 |

FOREIGN PATENT DOCUMENTS 0 676 638 A2  4/1995  European Pat. Off. .
0 713 080 A1  10/1995  European Pat. Off. .
WO 93/00570  1/1993  WIPO .

OTHER PUBLICATIONS

Giesler et al., *Sensors and Actuators B*, vol. B18, No. 1/3 (Mar. 1994), pp. 103–106, "Electrostatically Excited and Capacitively Detected Flexural Plate Waves on Thin Silicon Nitride Membranes With Chemical Sensors Applications".
Ramachandraiah et al., *Journal of Physics E. Scientific Instruments*, vol. 20, No. 1, (Jan. 1987), pp. 85–87, "An Ultrasonic Sing–Around System for Thin Solid Samples".
N.R. Karpov, Yu. D. Matyukhin, & N.N. Povarenkin, "Time–Interval Measurement by Regressive Coincidence" (01/80, *Instruments & Experimental Techniques*, pp. 1317–1318).
V.P. Voronov, V.M. Malyshev, & V.M. Merkulov, "Time–Delay Measuring Circuit for a Wave Pulse Used in Acoustic Experiments" (07/80, *Instruments & Experimental Techniques*, pp. 172–173).
R.A. Zakarevicius, E.H. Fooks & C.J.E. Phillips, "The Integrator as a Time Delay Estimator" (ICASSP 86, Tokyo, pp. 1861–1864) Arp. 1986.

*Primary Examiner*—Christine K. Oda

[57] ABSTRACT

A sensing apparatus includes a pulse recirculating circuit operatively connected to at least one ultrasonic delay sensor or other device for recirculating pulses therethrough, and a measurement difference output circuit for generating an output signal based upon a difference between first and second measurements of the at least one ultrasonic delay sensor. The pulse recirculating circuit preferably comprises a pulse generator for generating a series of input pulses to the ultrasonic delay sensor, and a pulse detector for detecting a series of output pulses after propagation through the ultrasonic delay sensor. Moreover, the measurement difference output circuit preferably includes an up-down counter for counting pulses during the first measurement in one direction and for counting pulses during the second measurement in an opposite direction. Accordingly, the remaining counter contents represent a difference in delay between the first and second measurements. Method aspects of the invention are also disclosed.

39 Claims, 11 Drawing Sheets

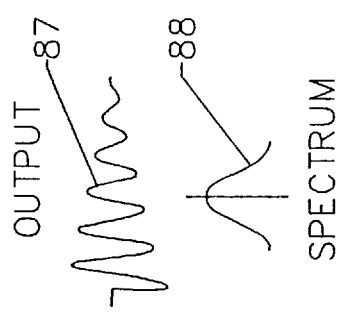
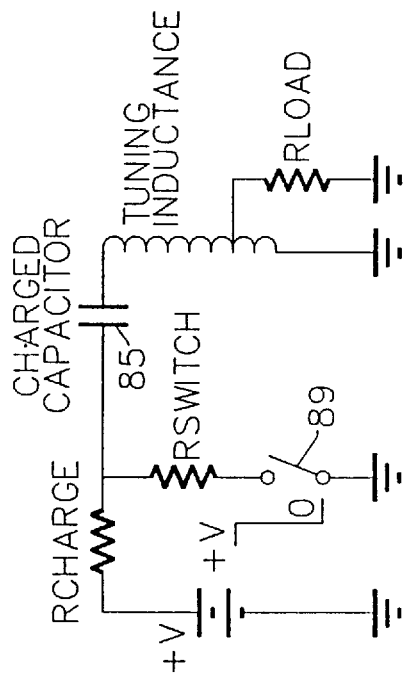
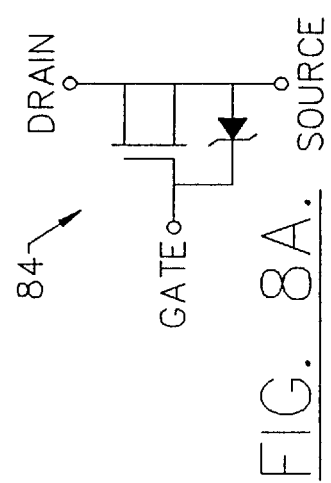
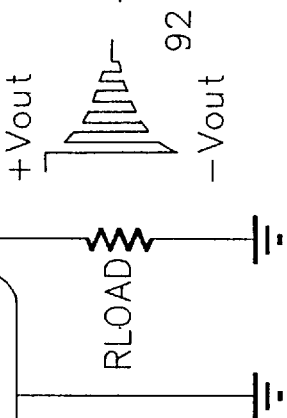
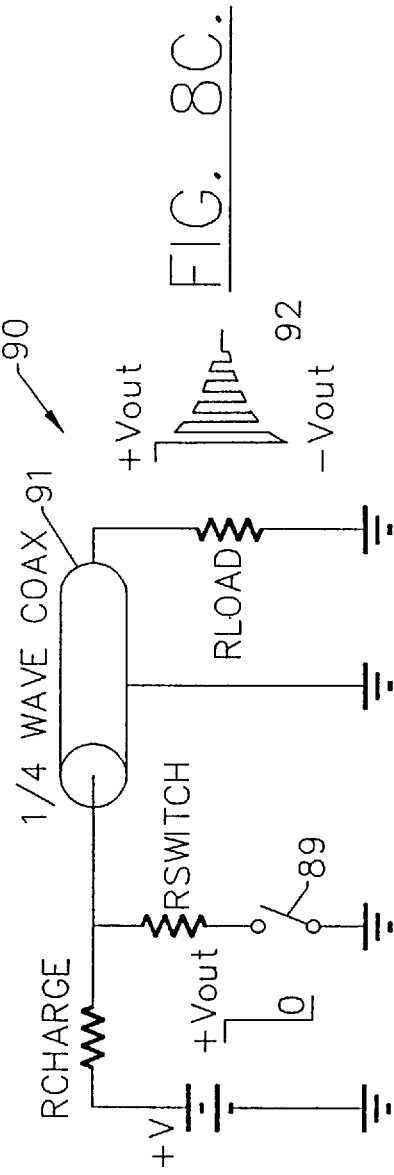
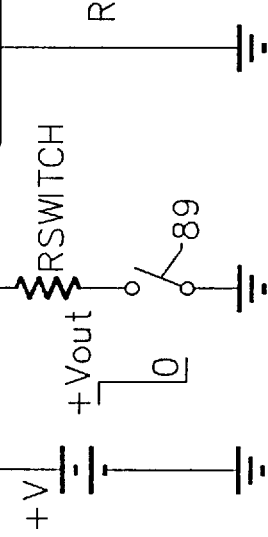

APPARATUS AND ASSOCIATED METHOD FOR MEASURING DIFFERENCES IN DELAY MEASUREMENTS

FIELD OF THE INVENTION

The present invention relates to the field of sensors and measurements, and, more particularly, to a measurement apparatus and associated method, such as for use with ultrasonic sensors and devices.

BACKGROUND OF THE INVENTION

Ultrasonic sensing devices, such as surface acoustic wave (SAW) vapor and pressure sensors, for example, typically require precise measurements of changes in acoustic velocity of signals propagating therethrough. For example, polymer coated SAW vapor sensors typically experience a change in acoustic velocity responsive to exposure to a chemical in the gas or liquid phase. In addition, it may be desirable to generate an output signal, based upon the change in acoustic velocity, that reflects the sensed chemical concentration, as disclosed, for example, in U.S. Pat. No. 5,076,094 to Frye et al. entitled "Dual Output Acoustic Wave Sensor for Molecular Identification", and U.S. Pat. No. 5,235,235 to Martin et al. entitled "Multiple-Frequency Acoustic Wave Devices for Chemical Sensing and Materials Characterization in Both Gas and Liquid Phase".

Another common use for a SAW sensor includes pressure measurement, where changes in pressure are correlated to changes in acoustic velocity of the sensor as disclosed in U.S. Pat. No. 4,534,223 to Sinha et al. and entitled "Surface Acoustic Wave Sensors". SAW devices are also used for particulate sensors, fluid flow sensors, temperature and acceleration sensors, and many other types of sensors.

A SAW sensor may also be selectively responsive to a predetermined chemical. Accordingly, a plurality of SAW sensors may be combined in a single apparatus for sensing respective vapor concentrations as disclosed, for example, in U.S. Pat. No. 4,895,017 to Pyke et al. and entitled "Apparatus and Method for Early Detection and Identification of Dilute Chemical Vapors." Similarly, U.S. Pat. No. 5,012,668 to Haworth entitled "Inclined Electrode Surface Acoustic Wave Substance Sensor" also discloses a chemical sensing apparatus including a plurality of SAW sensors wherein output signals from a substance sensor and a reference SAW device are compared in a mixer and the output signals are time multiplexed. Along these lines, U.S. Pat. No. 5,325,704 to Mariani et al. entitled "Surface Acoustic Wave (SAW) Chemical Multi-Sensor Array" discloses a plurality of pairs of SAW sensors and reference devices so that exposure to the sensed chemical causes a difference in acoustic velocity between the SAW sensor and reference SAW device.

When it is desired to measure small changes in acoustic velocity, such as with an ultrasonic sensor, conventional techniques may use the sensor as a frequency control element in an oscillator, such as commonly done with polymer coated SAW vapor sensors. Occasionally, two oscillators are used, one for a reference element, and the other for the ultrasonic sensor. Also, various direct means of measuring the insertion phase and loss have been used.

Problematic with such approaches are the fact that they are steady-state measurements, which are subject to any and all static error mechanisms. In SAW sensors, it is common for the insertion loss, band-shape, and multiple reflections to experience significant changes with exposure to the measured variable. These variations may induce significant errors. For example, as the insertion loss in the sensor changes, AM/PM conversion in an oscillator's sustaining device (amplifier) will become a factor in governing the frequency of oscillation. In addition, the change in gain compression may cause terminal impedance changes which may interact with tuned circuits, such as phase shifters and the measuring device matching networks.

Consider that the following are representative of a specific polymer coated SAW vapor sensor. A representative 100 MHz, 2.5 $\mu$S SAW vapor sensor will experience roughly $7.5 \times 10^{-4}$ degrees of phase shift for each 1 PPM of a specific vapor concentration. Since it is desired to measure at and below this level, one need only recall that this imposes a severe constraint on the electronic circuit (both active and passive) insertion phase stability. If direct insertion phase measurements are to be used, the phase detector AC and DC offsets are large compared to the sensor sensitivity.

Often it is desired to measure with an array of vapor sensors with each one responsive selectively to certain compounds—a common requirement in public safety and environmental compliance testing. In these cases, since the measured variables are relatively small, the only practical means of avoiding corrupting interaction of the electronic signals may be through frequency diversity, which is seriously complicating to a CW measurement system. Indeed, it can be a prohibitive cost-driver.

Particularly with public safety and remote site sensor applications, power consumption is a critical concern since many of these applications require battery powered equipment. Additionally, it is often required that public safety equipment be hand-held, implicating size, weight, and durability issues, as well.

SUMMARY OF THE INVENTION

In view of the foregoing background, it is therefore an object of the present invention to provide an apparatus and method for performing measurements of ultrasonic sensors to have high resolution, low granularity, good linearity, and high throughput, without incurring significant cost, complexity, and power consumption penalties.

These and other objects, advantages and features of the present invention are provided by an embodiment of a sensing apparatus according to the invention including time domain analysis means operatively connected to an ultrasonic delay sensor for recirculating pulses therethrough and for generating the output signal related to the sensed quantity. In particular, the time domain analysis means may preferably comprise pulse generator means for generating a series of input pulses to the ultrasonic delay sensor; pulse detector means for detecting a series of output pulses after propagation through the ultrasonic delay sensor; and pulse recirculating means for causing the pulse generator means to generate the series of input pulses based upon respective previously detected output pulses from the pulse detector means.

The ultrasonic delay sensor may be of the type that generates undesired multiple reflections from pulses propagating therethrough. Accordingly, the time domain analysis means may preferably include reflection suppression means for suppressing the undesirable reflections generated by the ultrasonic delay sensor. The reflection suppression means may be provided by random phase switching means cooperating with the pulse generator means for randomly switching phases of the series of input pulses to the ultrasonic delay sensor to thereby reduce undesired reflections. In addition, the reflection suppression means may also include a fixed delay operatively connected between the pulse detector means and the pulse generator means.

The reflection suppression means may also further comprise time diversity matching means operatively connected between the pulse generator means and the ultrasonic delay sensor for providing a substantial conjugate match therebetween during a time interval of each pulse and providing a relatively large mismatch at other times.

The recirculating delay measurement permits time displacement of the desired response with much lower magnitude time spurious than would otherwise be the case, and also permits time diversity matching wherein a conjugate match to the sensor transducer is provided over the drive pulse interval and a near short-circuit is presented at all other times thereby providing a high degree of time spurious suppression.

Another aspect of the present invention is that because time domain analysis is used to measure delay, the apparatus may include time division multiplex means for successively connecting the time domain analysis means to each of a plurality of ultrasonic delay sensors. Accordingly, the time domain analysis means may generate a plurality of output signals related to corresponding sensed quantities.

The sensing apparatus has particular applicability to the measurement of surface acoustic wave (SAW) vapor sensors. Accordingly, the time domain analysis means may further comprise vapor concentration output means for generating the output signal related to vapor concentration sensed by the SAW vapor sensor. In addition, the vapor concentration output means may further include sensor calibration means for calibrating the output signal. Alternately, the ultrasonic delay sensor may be an ultrasonic delay pressure sensor, and the time domain analysis means may further comprises pressure output means for generating the output signal related to pressure sensed by the ultrasonic delay pressure sensor. Other ultrasonic delay devices, such as a SAW particulate sensor among others, may also be advantageously measured by, or incorporated into, various embodiments of the present invention.

The time domain analysis means may preferably include time base means for generating a time base signal having a predetermined time base period. Thus, the time domain analysis means may comprise counting means for determining a number of time base periods occurring during a measurement defined by a predetermined number of pulse recirculations. Moreover, the apparatus may further comprise integration means cooperating with the time base means for generating an interpolation signal based upon constant rate integration relative to a predetermined time period of the time base.

The regeneration of the detected, delayed pulse, and recirculation thereof a relatively large number of times causes the accumulation of a small delay change to result in a much larger period of time. At the same time, randomly alternating the starting polarity of the pulse generator renders the regenerated pulse starting phase statistically independent of that of previous pulses causing the phase of multiple reflections to be statistically independent as well. Because the reflections statistically sum to zero, there is no need to wait for the reflections to dissipate before starting the next measurement, thereby allowing the measurements to be continuous.

A method aspect of the present invention is for measuring delay of an ultrasonic delay device and includes the steps of: recirculating pulses through the ultrasonic delay device; and generating an output signal related to the delay of the ultrasonic delay device. The step of recirculating pulses through the ultrasonic delay device may include detecting a series of output pulses after propagation through the ultrasonic delay device, and while generating the series of input pulses based upon respective previously detected output pulses.

The method also preferably includes the step of suppressing undesirable reflections generated by the ultrasonic delay device by randomly switching phases of the series of input pulses to the ultrasonic delay device and/or by inserting a fixed delay in a pulse recirculating path. The step of suppressing undesirable reflections also preferably includes the step of providing a substantial conjugate match between a pulse generator and the ultrasonic delay device during a time interval of each pulse and providing a relatively large mismatch at other times. Time division multiplexing may be used to interface with a plurality of ultrasonic delay devices, such as SAW vapor or particulate sensors.

BRIEF DESCRIPTION OF THE DRAWINGS

FIGS. 8A, 8B and 8C are schematic diagrams of pulse generator circuits that may be incorporated in the apparatus in accordance with the invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
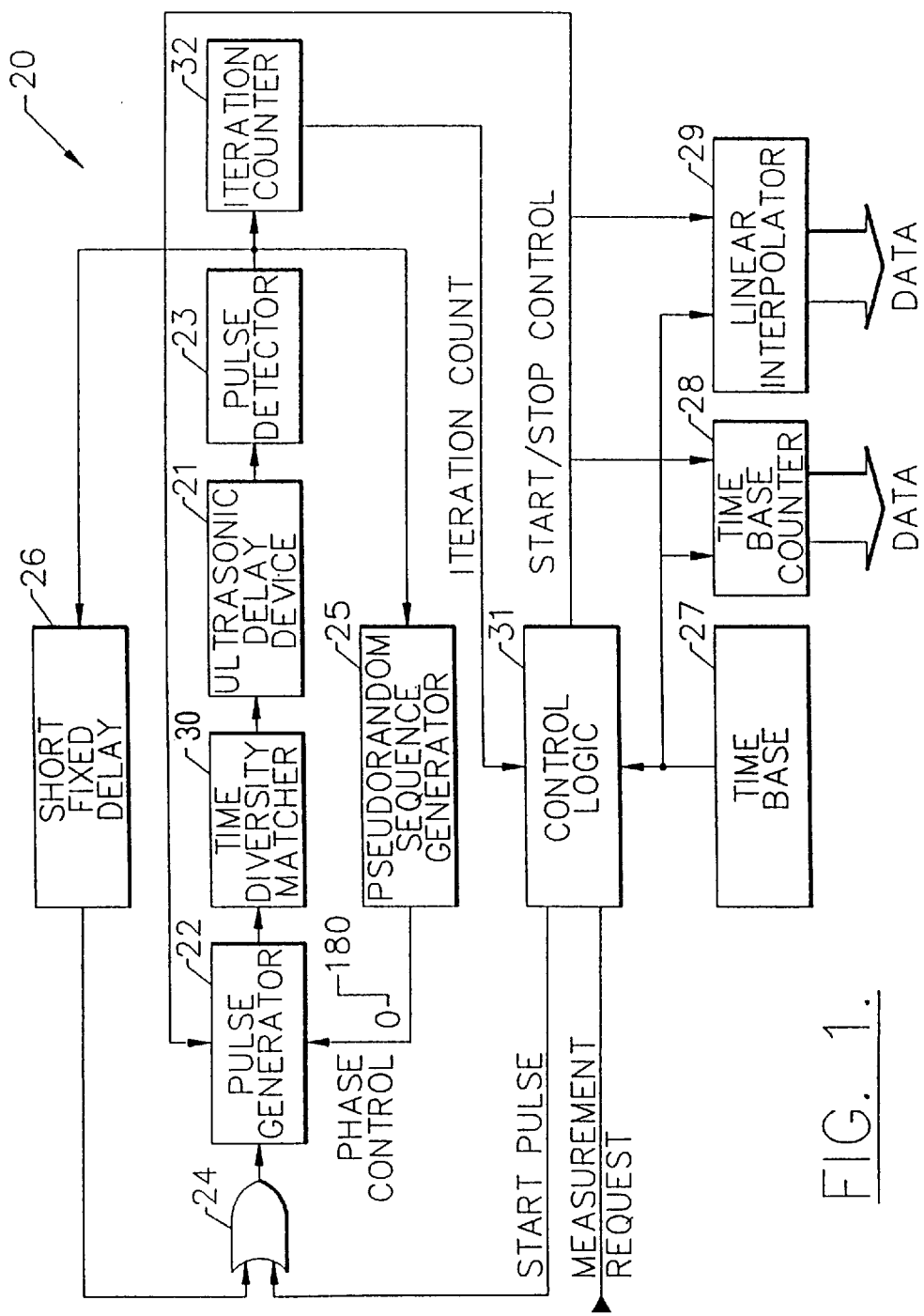
FIG. 1 is a schematic block diagram of an embodiment of the apparatus in accordance with the present invention.

Referring now to FIG. 1, a first embodiment of the apparatus 20 according to the invention is described. The apparatus 20 includes time domain analysis means operatively connected to the ultrasonic delay sensor or delay device 21 for recirculating pulses therethrough and for generating the output signal related to the sensed quantity. As would be readily understood by those skilled in the art, the ultrasonic delay device 21 may be a sensor having a delay related to the sensed quantity, such as a SAW vapor, particulate, or pressure sensor.

In the illustrated embodiment, the time domain analysis means comprises pulse generator means 22 for generating a series of input pulses to the ultrasonic delay sensor 21. Pulse detector means 23 is positioned downstream from the ultrasonic delay device 21 for detecting a series of output pulses after propagation through the ultrasonic delay device. In addition, pulse recirculating means is provided for causing the pulse generator means 22 to generate the series of input pulses based upon respective previously detected output pulses from the pulse detector means 23.

The ultrasonic delay sensor 21 may be of the type that generates undesired multiple reflections from pulses propagating therethrough. Accordingly, the time domain analysis means may preferably include reflection suppression means for suppressing the undesirable reflections generated by the ultrasonic delay sensor 21. The reflection suppression means may be provided by random phase switching means, such as the illustrated pseudorandom sequence generator 25 cooperating with the pulse generator means 22, for randomly switching phases of the series of input pulses to the ultrasonic delay sensor 21 to thereby reduce undesired reflections.

In addition, the reflection suppression means may also include a short fixed delay 26 operatively connected between the pulse detector means 23 and the pulse generator means 22 by the illustrated logic gate 24. This permits time displacement of the desired response relative to the undesired multiple reflections of prior responses resulting in much lower magnitude time spurious than would otherwise be the case. The reflection suppression means may also further comprise time diversity matching means 28 operatively connected between the pulse generator means 22 and the ultrasonic delay sensor 21 for providing a substantial conjugate match therebetween during a time interval of each pulse and providing a relatively large mismatch at other times and thereby providing a high degree of time spurious suppression.

The illustrated apparatus 20 also includes a time base 27 and associated time base counter 28 cooperating with control logic 31 and the illustrated iteration counter 32 to produce an output signal related to the delay of the ultrasonic delay device 21.

The terms "delay device" or "delay element" or similar phrases, includes any and all ultrasonic delay elements. The term "pulse generator" includes any transient waveform generator. The term "pulse detector" may be any device, circuit, or combination thereof that results in a distinct output change as a result of an input signal going above or below a certain level, such as a threshold. The threshold may be fixed, or a fraction of the input signal level. The term "pulse detector" includes, but is not limited to, analog comparators, negative resistance devices and/or circuits used as analog level detectors, Schmidt trigger circuits, etc. The term "pulse detector" also includes, but is not limited to, any ancillary device, circuit, or pre-processing, used, such as an RF magnitude detector, coherent detector, or complex demodulator, from which the RF magnitude or squared magnitude is derived, and also includes any filters, integrators, amplifiers, and transducers used.

As would be readily understood by those skilled in the art, any part or all of the described logic functions and operations described herein may be performed by a micro-controller, micro-computer, programmable logic array, etc. without departing from the scope and spirit of the invention. Where indicated, a JK bistable may be any functional equivalent, be it a D type bistable, master-slave bistable, or other equivalent. A monostable circuit may be any device or circuit that has as its output a discrete pulse that is the response to an input level change in a predetermined direction. This term contemplates either an analog or digital input.

The term "up-down counter" refers to any counter that can reverse its counting mode, either synchronously or asynchronously, be it presettable or not, be it a binary counter, binary coded decimal (BCD) counter, or a counter operating on any other radice, and includes any other counting method, be it two-level or multi-level, and also includes any precounter or prescaler. The term "up-down counter" includes any logic family, such as, but not limited to, TTL, Schottky TTL, CMOS, ACMOS, or any logic family providing functionally equivalent devices and/or combination of devices and contemplates functional implementation in any micro-controller, micro-computer, or programmable logic array.

Discussion of features and issues related to ultrasonic devices and properties do not preclude the invention from measuring any other type of delay element.

There are several subtle but important advantages to be gained by regenerating and recirculating a pulse that has propagated through a delay element 21, as in the illustrated apparatus 20 of FIG. 1. The pulse generation/recovery process can be reiterated and counted a predetermined number of iterations. This process "expands" the delay interval by a factor equal to the number of iterations. For example, $10^6$ iterations through a 2.5 $\mu$S delay path takes a total of 2.5 seconds.

Now, suppose that this delay represents a SAW sensor that has experienced a 1 pS delay change from a previous measurement, for any of a variety of reasons, such as exposure to a chemical vapor. The total period for $10^6$ iterations is now 2.5 seconds plus 1 $\mu$S ($10^{-12} \times 10^6$). The 1 $\mu$S time expansion is easily resolved with low power logic such as ACMOS. In the case of a 10 MHz time base, the 100 nS time base interval now represents 0.1 pS measurement granularity.

This is an important property of the present invention since it states, in effect, that the weight of the time base interval has been divided by the number of iterations. This applies to any interpolation as well. Furthermore, unlike in prior art, interpolation need only be performed once, after the last iteration, thus greatly relieving the interpolation circuit performance requirements.

For another example, less than 10 pS granularity is achieved in 100 iterations with a 10 MHz time base interval and the next time base pulse and an 8 bit A/D converter used for the interpolation of constant rate integration between the end of the delay interval occurring immediately thereafter. For the previously discussed 2.5 $\mu$S delay element, the measurement time is 250 $\mu$S plus an additional 10 to 20 $\mu$S for the interpolating A/D.

One of the many important benefits gained by the present invention is that the much shorter measurement time greatly relieves the short term stability requirements of the measurement system circuitry, including the time base 27. Another important benefit, because of the moderate time base frequency, is that inexpensive, low power logic and other circuitry can be used.

One of the most important benefits is that, almost always, the granularity will converge to a desired resolution limit faster than any noise averaging that might be desired. Put another way, it is almost always the case that the measurement apparatus 20 of the present invention can be configured so that granularity will not limit the measurement resolution.

Now, if a stable delay element similar to delay device 21 is used as a reference delay line, it is possible to use an up/down counter to perform the subtraction of the invariant part of the total delay, simply by counting the DUT delay and down-counting the reference delay. The remaining counter contents represents the delay difference between the two delay elements. In fact, the counter range needs only to be large enough to accommodate the longest anticipated delay difference, since it will "wrap-around" in up-counting and "unwrap" the same amount in down-counting, with the remaining contents being the desired measurement residual.

Similarly, the initial delay measurement of a delay element can be stored and subsequently subtracted, such as with a presettable up/down counter, from later measurements to measure delay changes in a single delay element, such as might be desired in stability testing.

Figure 2:
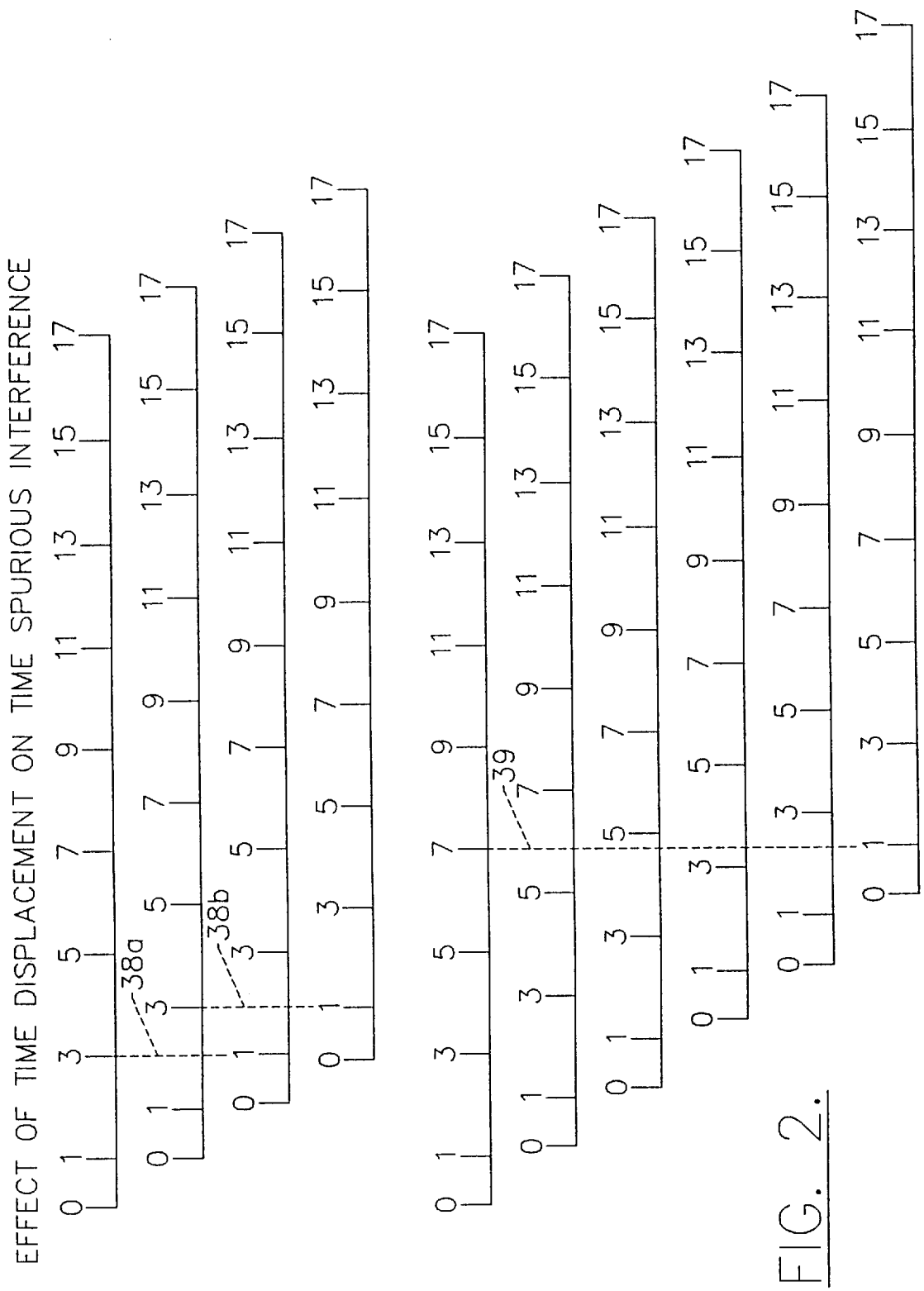
FIG. 2 is a timing diagram of pulses and spurious interference produced by the apparatus of FIG. 1.

In the case of 21, theasonic delay element 21, the recirculating pulses will sum with multiple reflections, such as triple travel as indicated by the dotted vertical lines 38a, 38b in FIG. 2. In the case of measuring ultrasonic device delay changes, the multiple reflections experience R times the delay change of the desired response. In other words, the Rth reflection "slides under" the desired impulse response. As it does so, the Rth reflection carrier phase changes with respect to the carrier phase of the desired pulse response, thereby creating constructive and destructive summation of the two carriers.

Figure 3:
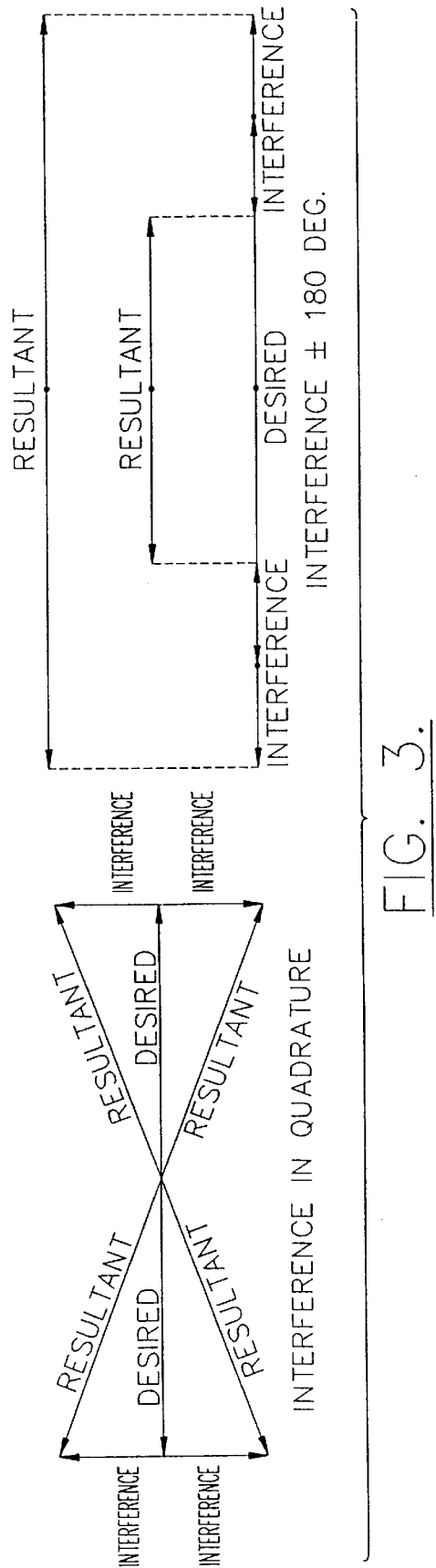
FIG. 3 is a diagram of possible vector relationships for the real and quadrature components of time spurious signals in accordance with the present invention.

Now, if the total recirculation delay is sufficiently different by a small and non-integer multiple or fraction of the ultrasonic delay, succeeding pulses will be displaced in time so that they will coincide only with higher order reflections, which are much lower in amplitude, as shown by the lower dotted vertical line 39 in FIG. 3. In many cases, the total circuit propagation delay will produce the desired time displacement. If not, a short fixed delay can be introduced, such as from an LC or coaxial delay line. Since this delay can be in common to both the reference and/or initial delay measurement, as in the case of measuring delay changes, it need only be stable over the measurement interval, which can be short relative to electronic circuit thermal time constants.

Because the ultrasonic pulse response has non-zero wavefront rise time (finite rate of rise), we are concerned about apparent delay changes due to variations in the detected pulse amplitude at the pulse detector 23 threshold level as caused by Rth travel time spurious. In measuring delay change, these errors may result in variations around the average delay trend line.

Evaluation of the desired and undesired vector relationship will determine the envelope amplitude variation experienced with ultrasonic device delay change. The vectors, represented in rectangular form, are shown in FIG. 3. The carrier resultant from quadrature interference is the square root of the sum of the square of the desired response carrier vector and the square of the time spurious carrier vector. An in-phase (or 180° out of phase) time spurious carrier vector adds or subtracts directly to the desired response carrier vector.

A commonly used rule for multiple reflections in SAW devices 21, such as may be used for delay devices, states that the magnitude of time spurious, in dBc relative to the desired response, decreases in dB twice as much as the insertion loss for each round trip. For example, if the insertion loss is 20 dB, the triple travel (delay plus one round trip) is 40 dBc, 5th travel (delay plus two round trips) is 80 Dbc, 7th travel (delay plus three round trips) is 120 dBc, and so on. Other ultrasonic devices 21 follow a similar pattern.

Frequently, as is the case of polymer coated SAW vapor sensors, the time spurious can be much worse than conventionally fabricated ultrasonic devices, since conventional reflection suppression techniques cannot typically be used for SAW vapor sensors. This discussion will start with the assumption of 20 dBc triple travel. The previously mentioned time displacement can result with the delayed sensor impulse response coinciding with the 7th travel time spurious, as shown by the dotted line 39 in FIG. 2, which, in this case, will be 60 dBc. For a desired response vector normalized to 1.0 volt peak, the magnitude of the time spurious vector will be 1.0 mV peak.

For the sake of discussion, assume a SAW vapor sensor 21 has two unweighted transducers with a null bandwidth of 4 MHz and further assume a nominal delay of 2.5 $\mu$S. The idealized impulse response of this device will be an equilateral triangular pulse with a 1.0 $\mu$S base width. For a peak amplitude normalized to 1.0 volts, the wavefront rate of rise is $2\times10^6$ volts/second. If the pulse detector threshold is set at 0.5 volts, the total pulse envelope variation due to an in-phase time spurious of 60 dBc will be 1.0 mVPP at the threshold level, resulting in a 0.5 nSPP time variation in crossing the pulse detector threshold. The desired response magnitude variation due to a time spurious carrier in phase quadrature with the desired response carrier will be $[(0.5V^2 + 1.0 mV^2)^{1/2} - 0.5V]$ or 1 uVPP, resulting in a pulse detection time variation of 0.5 pSPP.

As will be readily appreciated by those skilled in the art, the effect of in-phase time spurious is far more significant than that due to time spurious in phase quadrature. This is fortuitous since quadrature interference can only be reduced by increasing the ultrasonic device insertion loss. Nevertheless, trading off insertion loss, that is, noise, against time spurious can be highly advantageous. In the case of SAW devices, the relationship between the change in 7th travel time spurious level, in dBc, and insertion loss is 6 times, in dB, for each dB increase in insertion loss. Thus the previously given example of 0.5 nSPP for in-phase times spurious becomes 15.8 pSPP for a 5 dB increase in SAW device insertion loss. The quadrature interference is reduced from 0.5 pSPP to 0.5 fSPP for the same 5 dB increase in insertion loss. A more complete tabulation appears below in Table 1. Fortunately, the much larger in-phase induced errors can be reduced without an increase in insertion loss as described below.

TABLE 1

Delay Measurement Errors Due to Time Spurious

| R = 3 Reflections | R = 7 Reflections | In-phase Interference for R = 7 | Quadrature Interference for R = 7 |
|---|---|---|---|
| 20 dBc | 60 dBc | 0.5 nSPP | 0.5 pSPP |
| 30 dBc | 90 dBc | 15.8 pSPP | 0.5 pSPP |
| 40 dBc | 120 dBc | 0.5 pSPP | $5 \times 10^{-19}$ S |

Inspection of the vector diagram in FIG. 3 reveals that, if a method were used that resulted in the interfering vector having zero mean value over a plurality of measurements, the averaged value of the desired vector over time would be precisely that of the desired plus interfering vector without interference. Accordingly, one solution would be to switch the waveform polarity alternatively. Unfortunately, this will not help since, for some value of R reflections, one will discover that the desired and undesired vectors will be in a constant polarity relationship. With any repetitive sequence of carrier phase reversals, there will always be a value of R for which a constant phase relationship exists between the desired and undesired responses.

However, if the carrier phase of the desired response is rendered statistically independent of that of the Rth reflection carrier phase, averaging many such measurements will produce the desired results. A means to this end is to randomly switch the starting phase of the drive pulse ±180°.

One means of generating a pseudorandom sequence is represented by a shift register with the output of the last two registers summed by modulo 2 addition (the operation performed by an exclusive OR gate) with the modulo 2 sum fed back to the shift register input. Other feedback schemes can be, and frequently are, used to generate a pseudorandom sequence. When it is first powered up, its bistable circuits can randomly assume one of the two states. If the shift register is sufficiently long it is virtually guaranteed that its internal states are not all "1's" or "0's". If somewhat shorter, a second exclusive OR gate can be used in the feedback path, forcing the feedback signal to be complemented should another gate sense more than a predetermined number of adjacent registers in the same state.

Since a large number of measurement iterations is desirably used for time expansion and noise averaging, a pseudorandom sequence generator 25 may be ideally suited for randomizing the drive pulse polarity. The generator can be configured to have a pseudorandom sequence length longer than, and a non-integer multiple of, the measurement sequence, and therefore its output will be random to the measurement system. As would be readily appreciated by those skilled in the art, relatively simple circuits can perform the random polarity switching.

Table 2 below shows that pseudorandom drive polarization and averaging will reduce the effects of in-phase time spurious to levels comparable to those of averaged noise.

TABLE 2

Pseudorandom Recirculating Delay Resolution (RMS)

| R = 3 Reflections | R = 7 Reflections | $N = 10^5$ Iterations R = 7 | $N = 10^6$ Iterations R = 7 | $N = 10^7$ Iterations R = 7 |
|---|---|---|---|---|
| 20 dBc | 60 dBc | 1.58 pS | 0.5 pS | 0.16 pS |
| 30 dBc | 90 dBc | 50 fS | 15.8 fS | 5 fS |
| 40 dBc | 120 dBc | 1.58 fS | 0.5 fS | 0.16 fS |

The pulse amplification/recovery process may result in the introduction of noise mechanisms that may cause measurement jitter. As the recirculation progresses, any jitter will add as a mean square with each iteration. However, the delay adds directly, so the measurement jitter is reduced by a factor of $\sqrt{N}$ relative to the measured delay, where N represents the total number of measurement iterations.

Referring again more specifically to FIG. 1, upon receipt of a measurement request signal, the control logic 31 generates a start pulse signal which is time aligned with the time base 27. At the same time the time base counter 28 is enabled. The start pulse signal triggers the pulse generator 22 which drives the delay element 21. After a period of time equal to the delay element, the pulse detector 23 output indexes the iteration counter 32 by one count and triggers the random sequence generator 25. Also, the pulse detector 23 output is fed back to the input OR gate 24 through the fixed delay line 26, thereby triggering the pulse generator 22. This process repeats for a predetermined number of iterations stored in the control logic 31, at which time the time base counter 28 is disabled.

At the same time that the time base counter 28 was disabled, the linear interpolator 29 enables a constant rate integrator which is subsequently stopped by the next time base pulse occurring after the start/stop control disabled the time base counter. The integrator output may be immediately converted by an A/D converter whose output is formatted to be a fraction of the value that is obtained by the constant rate integration over a complete time base interval.

Figure 4:
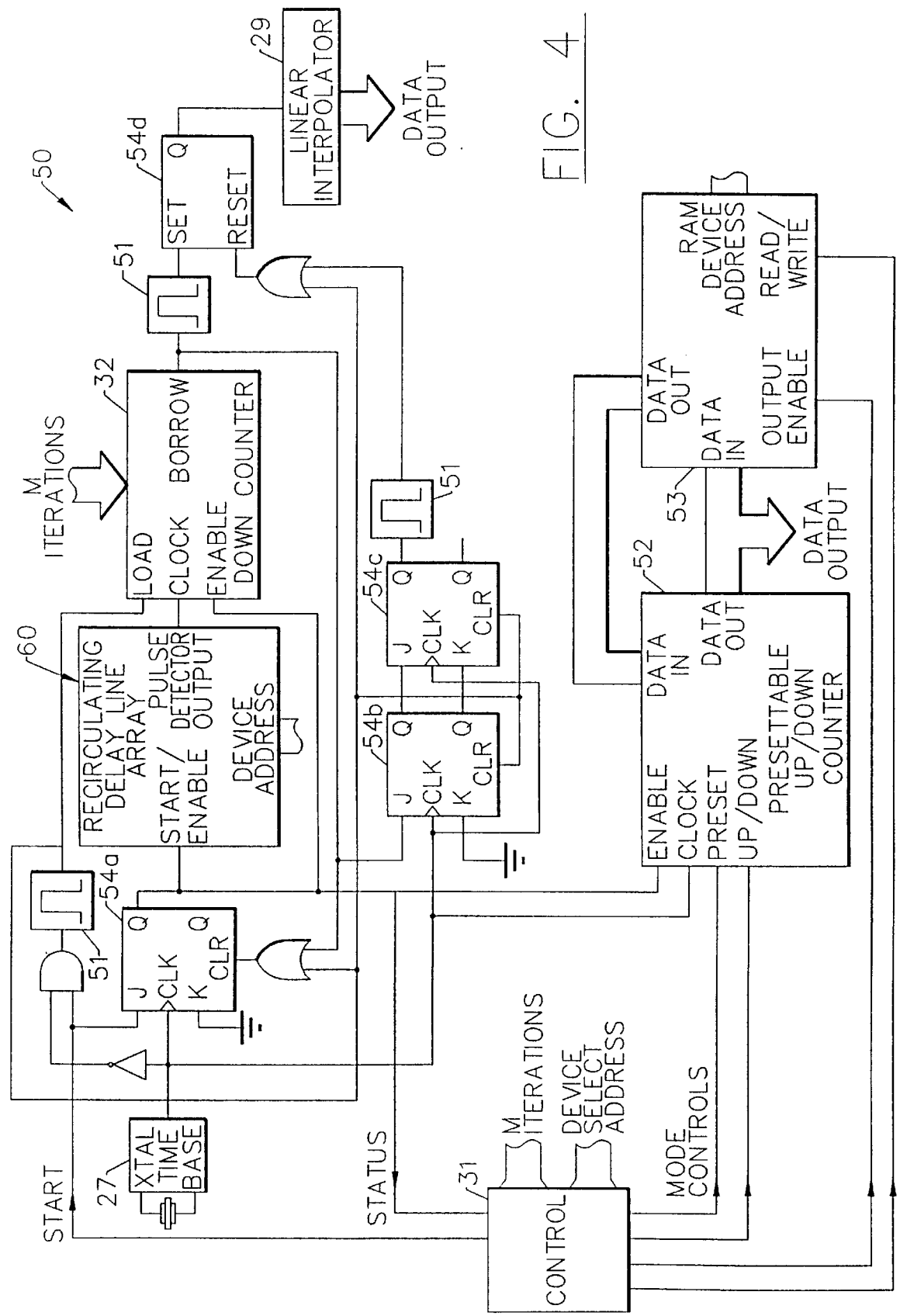
FIG. 4 is a schematic block diagram of portions of an embodiment of the apparatus in accordance with the invention including an array of SAW sensors.
Figure 5:
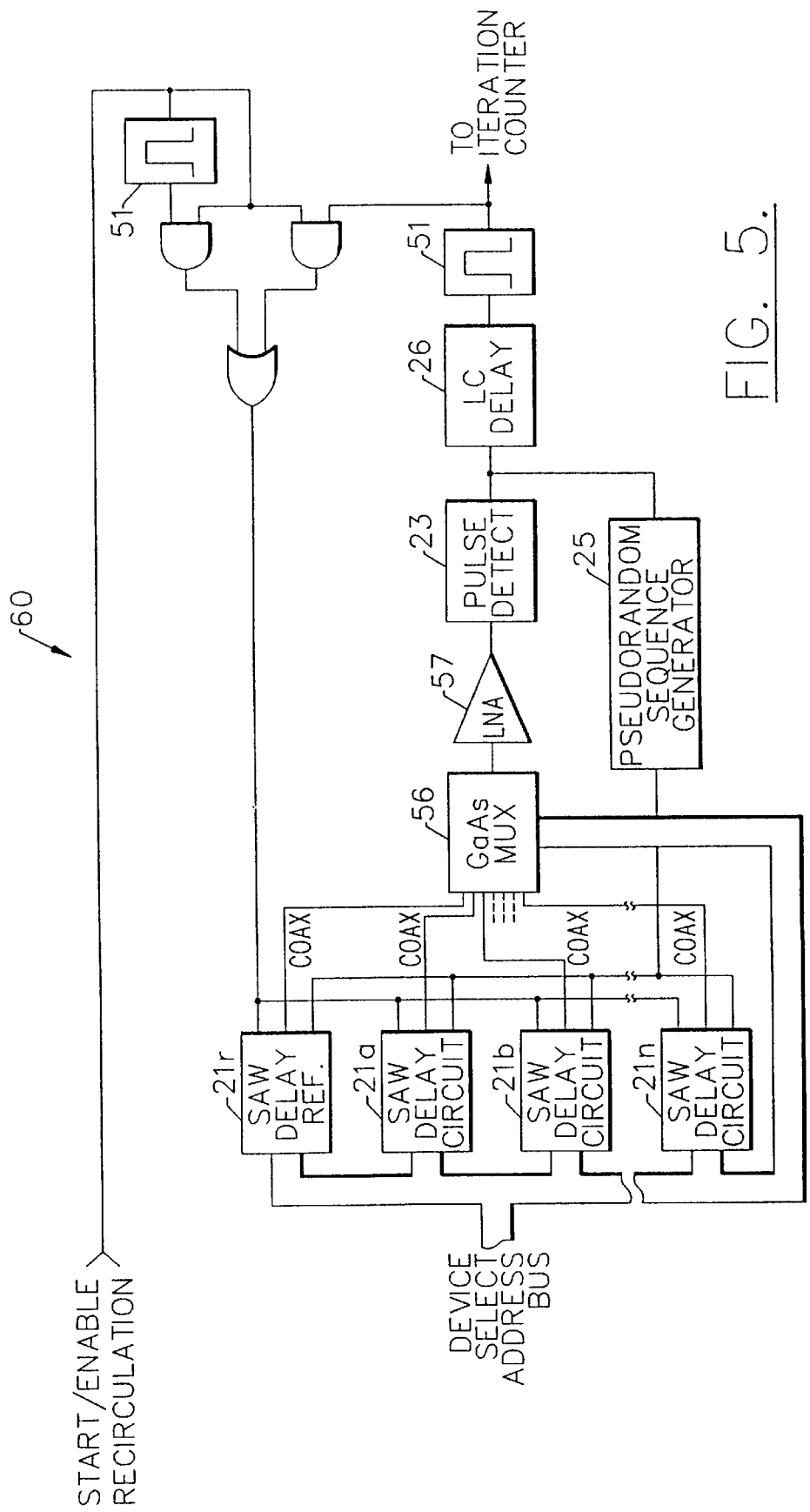
FIG. 5 is a schematic block diagram of a detailed portion of the apparatus as shown in FIG. 4.

A more detailed embodiment of the apparatus 50 according to the invention is understood with reference additionally to FIGS. 4 and 5. In this embodiment, measurements are being made on the recirculating delay line array 60 comprising SAW delay sensors 21a–21n as would be the case for SAW vapor sensing. It is assumed that the indicated control signals are being provided by a micro-controller or a simple state machine indicated by the controller 31, as would be readily understood by those skilled in the art. It is further assumed that the device select address lines and other control lines have settled before the application of a start pulse. The start pulse should be at least two time base periods wide to allow synchronization to the time base, but shorter than the nominal delay line length. The monostables 51 shown do not perform any time critical operations since the triggering action is always taken to be at the leading edge of the monostable output pulse.

As shown, the apparatus 50 has several possible operating modes as would be readily understood by those skilled in the art. In the interest of brevity, and for clarity, only one such operating sequence will be discussed herein. In this case, it is desired to measure the delay changes experienced by a plurality of delay lines which are SAW sensors 21a–21n as compared to the delay of the illustrated reference SAW device 21r.

Prior to a start pulse, the controller 31 has selected the "up" counting mode for the up/down counter 52, the scratch pad RAM 53 output is disabled, that is, all outputs are at logic "0", the read/write line is in the "read" mode, the number of iterations "M" has been selected, and the reference device address 21r is selected. Also, a pulse presets the up/down counter 52 to zero, since the RAM output was forced to zero. This is the equivalent of a reset.

The presentation of a start pulse generates a pulse when the clock (time base 27) output is low. This pulse resets all the bistable circuits (54a–54d) and loads "M" into the iteration down-counter. The next rising clock edge toggles bistable 54a Q output high, enabling both the iteration down-counter 32 and the up/down counter 52. It can be seen that bistable 54a also enables recirculation and generates the first drive pulse for the selected delay line, in this case, the reference delay line 21r. The GaAs MUX 56 and recovery circuits (low noise amplifier 57 and pulse detector 23) detect the delayed pulse, and, after a short delay for time displacement, cause the generation of another drive pulse. Each time a pulse is detected and regenerated, the iteration down-counter 32 is decremented by one count. At the same time the up/down counter 52 has, in this case, been counting time base pulses.

When the iteration counter 32 has decremented to zero, its borrow output is activated. This resets bistable 54a, disabling both recirculating and counting. The output of bistable 54a is also used as a status flag to indicate the end of the reiteration interval. The borrow output of the iteration counter 32 also sets bistable 54d, which is reset after the next two time base periods. The pulse width resulting at the output of 54d can be used in conjunction with a constant rate integrator for linear interpolation.

When the status line output of bistable 54a changes state, a write pulse is generated by the controller 31 and the contents of the up/down counter 52 are stored in the scratch pad RAM 53. The controller 31 selects another SAW device address and the up/down counter 52 down count mode is selected. In this case there is no need to issue a preset pulse since the counter 52 already contains the reference delay measurement value. A start pulse is then generated by the controller 31. The measurement sequence then continues as before. At the end of the measurement sequence, the up/down counter 52 now contains the delay difference between the reference delay 21r and the selected SAW delay element. This value can be stored for subsequent processing by issuing a write pulse for the selected address.

The original reference delay value can be reloaded into the up/down counter 52, if desired, simply by having the controller 31 select the reference address, enable the RAM output, and issue a preset command. Then the new address for another SAW array element can be generated and the process repeated for a second delay difference measurement, and so on.

Figure 6:
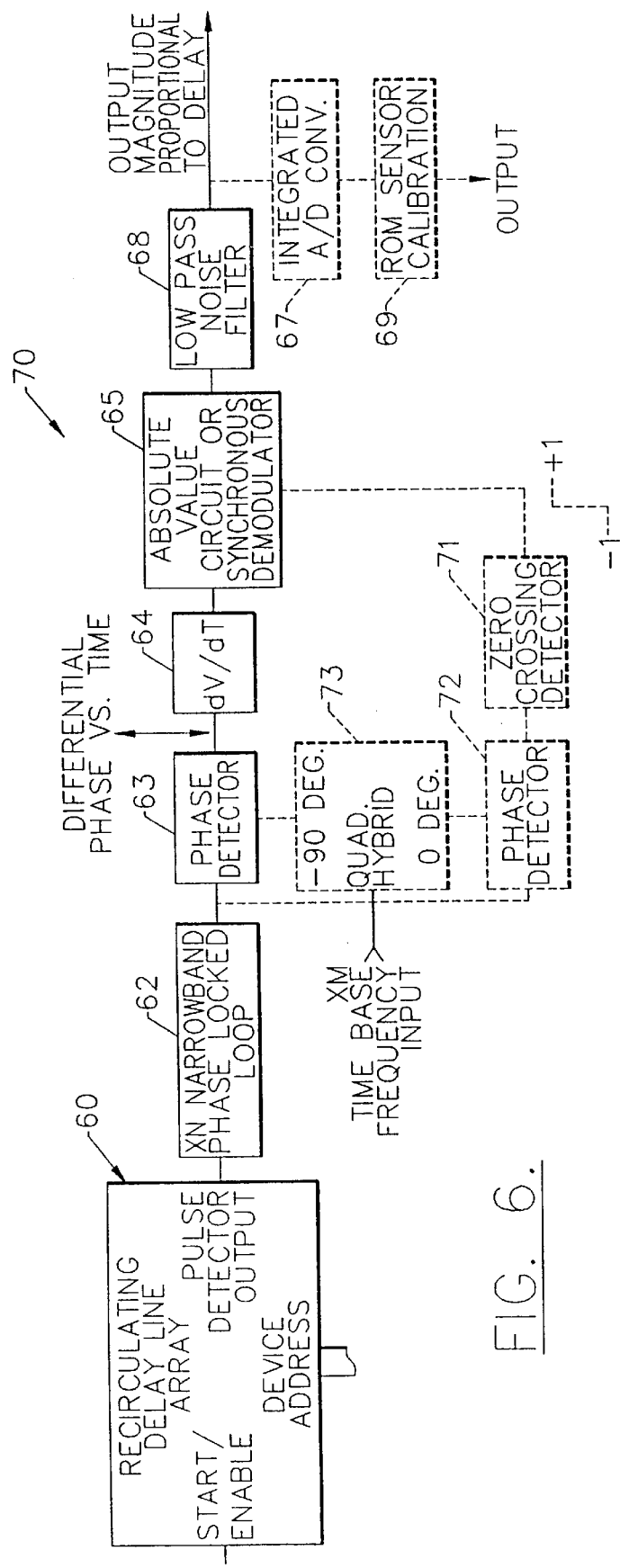
FIG. 6 is a schematic block diagram of a portion of another embodiment of the apparatus in accordance with the present invention for performing differential phase velocity (discriminator) measurement of delay.

Another important variation of recirculating delay measurement in accordance with the invention is schematically illustrated by the output circuit portion 70 of FIG. 6. Suppose, for the moment, that the nominal delay to be measured is 2.5 $\mu$S. This means that the recirculating pulse repetition frequency (PRF) is nominally 400 KHz. Assuming the same 10 MHz time base frequency, the time base is 25 times higher than the PRF. If the PRF is multiplied by this amount, the difference in phase velocity, that is, the frequency between the time base and the multiplied PRF will be related to any delay differences from, in this case, 2.5 $\mu$S.

For example, if the delay is exactly 2.5 $\mu$S, the PRF is exactly 400 KHz, which multiplied by 25 is exactly 10 MHz.

In this case, the differential phase velocity (frequency) is zero. Now, suppose the delay has increased by 1 pS. One finds that 25 times the new PRF is 4 Hz lower than 10 MHz, or 25.132 radians per second. This is found from the following equation:

$$\phi(t) = 2\pi \times \left( F_{timebase} - \frac{F}{\tau + \Delta\tau} \right) \text{Rad/Sec}, \qquad (1)$$

where F is a factor=integer [$F_{timebase}$PRF$_{nominal}$]. Usually $\tau$ is much larger than $\Delta\tau$ for SAW sensors, and $F_{timebase}$, by design, is very nearly equal the second term within the brackets, the result being that $\phi(t)$ is very nearly linearly related to $\Delta\tau$, even though the general form of the equation is non-linear.

In the simplest case, where noise is not a consideration, the phase detector 63 can be an exclusive OR gate and low pass filter. The output of the lowpass filter is fed to a phase differentiator 64, which, in turn, drives the absolute value circuit 65 and noise band limiting filter 68, the output of which represents a voltage analog of delay. When high resolution is required, a high detected signal-to-noise ratio is preferably maintained. In this case, the absolute value circuit 65 may preferably take the form of a synchronous demodulator (coherent detector). Synchronous demodulation avoids the rectification of noise that occurs in a non-coherent absolute-value circuit. Rectified (non-zero mean) noise will seriously limit sensitivity because the signal to noise ratio is defined in the full noise spectrum at the differentiator 64 output. Since the coherent-demodulator preserves its input noise statistics, the output noise is subject to the full effect of the noise band-limiting output filter 68.

The peak value of the derivative of the phase detector output occurs when the phase detector output is zero and is related directly to the phase detector gain constant and the time rate of change of phase. Both can be very accurately established with operational absolute-value and peak detection circuits, as would be readily understood by those skilled in the art.

The zero crossing detector 71, phase detector 72, and quadrature hybrid 73 provide a high resolution vernier circuit as would be readily understood by those skilled in the art. Now, if the time base signal is split into two outputs in phase quadrature, such as by quadrature hybrid 73, a second phase detector 72 can be used to provide a synchronous demodulation signal for the differentiator 64 output, since this signal will be phase shifted by +90 degrees relative to its input. Zero crossing detector 71 can be used to provide a hard-limited (polarity or sign-function) waveform for a synchronous demodulator 65. Since synchronous demodulation preserves the original noise statistics, the low pass filter 68 bandwidth can be set to provide, in theory, an arbitrarily long averaging interval.

Often, a digital output indication of delay is required, as is the case when a ROM sensor calibration table 69 is used. The output of the differential phase-velocity recirculating delay measurement circuit 70 is ideally suited for use with very inexpensive dual-slope integrating A/D's 67, which are ubiquitous commodities. In the differential phase velocity method, the noise band limiting of the multiplying phase locked loop (PLL) 62 and the output circuits, including the low pass filter 68 and the integrating A/D 67, will perform the equivalent of measurement averaging.

Figure 7:
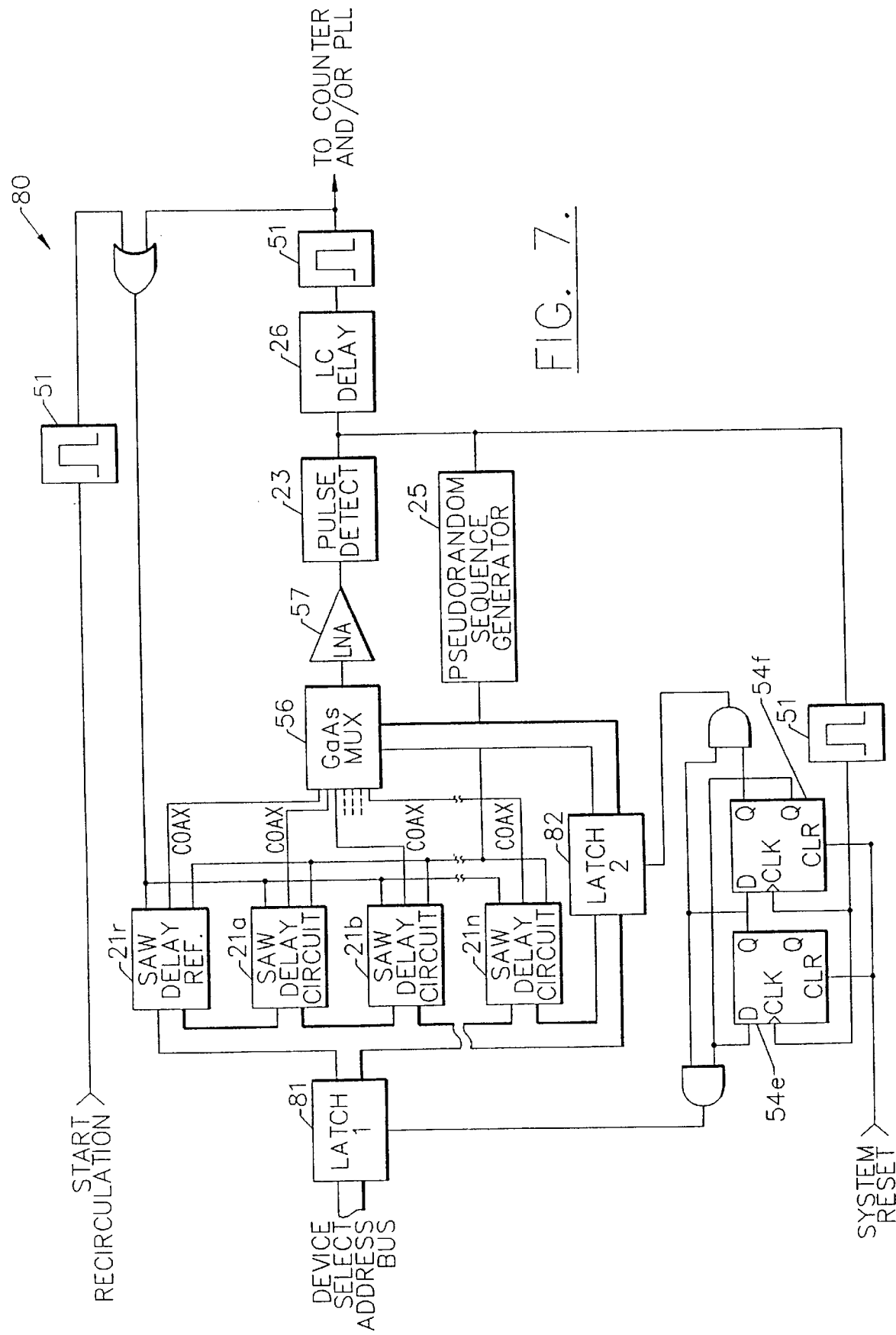
FIG. 7 is a schematic block diagram of yet another embodiment of the apparatus in accordance with the invention for continuous recirculating delay measurement of an ultrasonic device array.

Because of the time diversity, the array addresses can be switched between recirculating pulses as shown in the circuit portion 80 of FIG. 7. This arrangement permits asynchronous address switching and also corrects any data skewing on the address line. The address latch 82 for the GaAs MUX 56 is switched one recirculating delay pulse after the input latch 81 to derive a pulse from the last delay element address for the new delay element address. If the input and output addresses were switched simultaneously, a recirculating pulse can be lost, precluding continuous operation which is important for this mode of operation. As would be readily understood by those skilled in the art, D-type bistables 54e, 54f are also included in the circuit portion 70 and those components similar to those in FIG. 4 need no further description.

Again, if the output is quantized by an A/D, a scratch-pad RAM 53 (FIG. 4), with addresses corresponding to specific sensors, can be used to store measurements of individual sensors which may be subsequently compared to earlier measurements or to that of a reference sensor 21r which may or may not be coated. Those practiced in the art will recognize that the phase velocity or discriminator implementations of the recirculating delay measurement system are very powerful tools for low cost, low power, precision measurement of coated SAW sensor arrays.

The continuous recirculating delay phase measurement techniques have the advantage of simplicity, cost, and low power consumption. Recall that the multiplying phase lock loop 62 components are commodity items in various forms of CMOS integrated circuits. The oscillator in the multiplying PLL can be a very inexpensive, low power, VCXO using a consumer grade fundamental mode AT-cut crystal. Such a VCXO can operate at single milliampere current levels and easily achieve 5 KHz tuning range in the region of 10 MHz. If more tuning range is desired, a coupled-resonator frequency control element, such as a crystal filter can be used as shown in U.S. Pat. No. 5,196,811 the entire disclosure of which is incorporated herein by reference.

Those practiced in the art can readily ascertain that the counting method, previously described, and phase measurement method can readily be adapted for use together, if desired, typically with the phase measurement providing high resolution interpolation for the counted measurement. In all forms of recirculating delay systems, the pulse generation and detection operations are important since they will have a direct bearing on the measurement resolution. There are a large number of means to configure the pulse driver 22 (FIG. 1). One means will be discussed which is suitable for use with portable SAW sensor arrays.

For an ultrasonic delay element 21, the detected signal-to-noise ratio will depend on the energy available to the ultrasonic delay element, the insertion loss of the ultrasonic delay element, and the noise figure and noise bandwidth of the post delay recovery circuits. For the purposes of further discussion, a recovery amplifier noise figure of 3 dB will be assumed.

The pulse driver 22 must generate a low-energy, high peak amplitude, RF pulse. A desirable RF drive pulse spectrum is a compromise between energy efficiency and the SAW time response. If the pulse spectrum is too wide, the energy that is outside of the SAW passband is wasted, reducing the achievable detected signal-to-noise ratio and, therefore, measurement resolution. If the pulse spectrum is too narrow, the SAW time response will be too slow, increasing jitter in the pulse detector, also reducing the achievable measurement resolution.

Since DC power is typically at a premium, the SAW vapor sensor driver should be comprised of a reactive energy storage element and a fast-discharge control device. For efficient conversion of the stored energy to RF energy, the control element must switch in a small fraction of an RF carrier period. Historically this role has been relegated to step recovery diodes, tunnel diodes, and avalanche transistors, which remain the fastest switching devices (10's to 100's of pS). However, the use of these devices as pulse generators each involve complications that would be preferable to avoid as would be readily understood by those skilled in the art.

Because a SAW vapor sensor 21 can operate at lower frequencies ($\leq 200$ MHz), another control device technology, the DMOS FET becomes attractive, since GaAs FET switches cannot handle high peak signal levels at lower frequencies. DMOS is an acronym for the double-diffused metal oxide semiconductor. Like all field effect transistors, it is a majority carrier device whose switching speed is limited primarily by the time it takes to charge and discharge its interelectrode capacitances. Lateral DMOS transistors are capable of switching relatively high peak currents ($\approx 0.1$ to 1 amp.) in less than 1 nS. The lateral DMOS transistor is distinguished from other high-current MOS technologies by much lower terminal capacitance for equivalent transconductance and/or on-resistance (though it cannot handle as large average current, which is not of concern in this case). A representative DMOS FET device 84 as may be used for the pulse generator 22 of the present invention is illustrated schematically in FIG. 8A.

One method of generating an RF pulse is to store a DC voltage or current in a capacitor 85 or inductor that is subsequently switched by switch 89 to become part of a resonant circuit 86, that is, a tuned circuit with non-zero initial conditions as illustrated in FIG. 8B. The stored energy circulates in the resonant circuit and decays as governed by the circuit's time response, as shown by the waveform 87 in the upper right hand portion of FIG. 8B. Note in FIG. 8B the generated spectrum 88 (lower right hand portion) is identical to the band shape of the filter formed when the switch is closed. This filter may be a more complex structure, such as maximally flat filter, for improved spectral efficiency relative to the SAW sensor passband, as would be readily understood by those skilled in the art.

Another method for DC to RF conversion makes use of a circuit 90 including a charged quarter wave coaxial line 91, where the wavelength is defined as the EM wavelength at the SAW center frequency, as shown in FIG. 8C. The load is shown as DC-coupled to clarify the output waveform voltage relationships as shown by the waveform 92, although it can also be AC coupled, thereby allowing the coaxial line to charge the full supply voltage.

Both pulse generation circuits 86, 90 have proven to be attractive because of their simplicity and low average power requirements. Additionally, these circuits can readily be configured to provide impedance matching for the SAW sensors 21, that is, the pulse forming network may be imbedded in the matching network. Another important property of the switched discharge form of RF pulse generation is found in that the network can be designed to provide the optimum power transfer to the SAW transducer during discharge when the depicted switch 89 is closed, and a large mismatch when the switch is open. In other words, the switched discharge network represents a time variant source impedance. Since the generated pulse is usually much shorter than the ultrasonic delay, this property can be exploited to provide further time spurious suppression. It is a relatively simple matter to design the storage network to represent a substantial conjugate match during discharge and a near short when the switch 89 is open, as clearly implicated in the case of the charged quarter wave line 91. Lumped element networks can be designed with similar properties.

Figure 9:
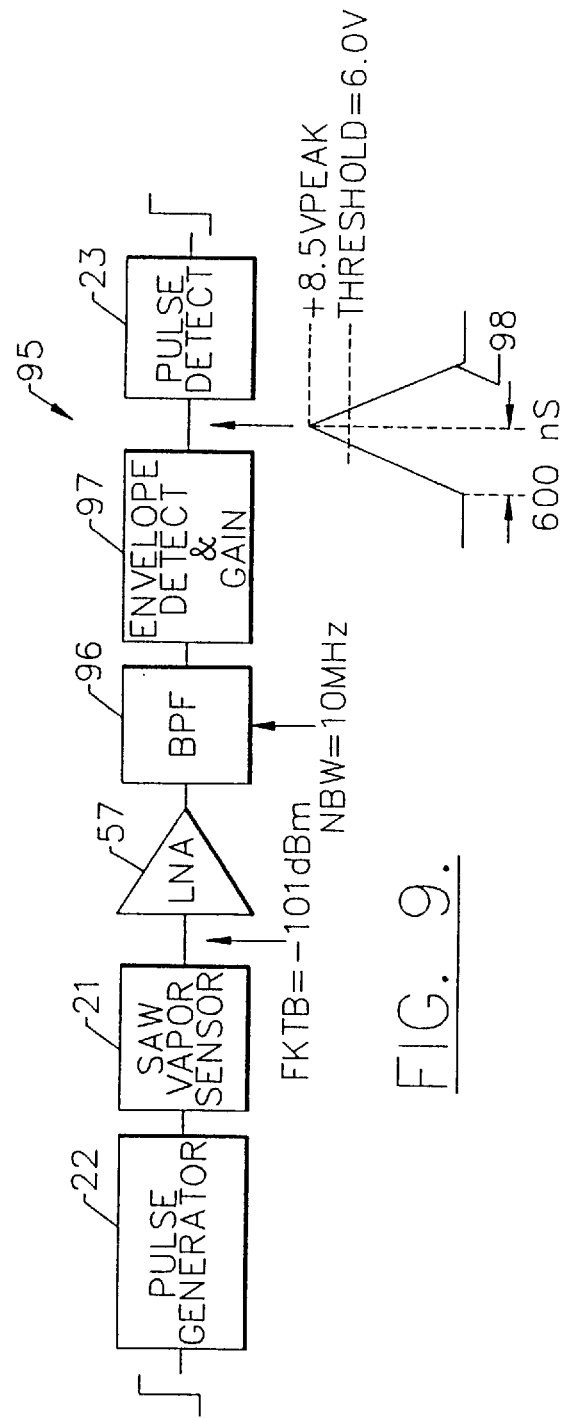
FIG. 9 is a schematic block diagram of a portion of an embodiment of the apparatus in accordance with the present invention and illustrating signal gain distribution therethrough.

In order to determine the energy storage requirement for the pulse driver, it will be desirable to examine the SAW sensor measurement channel gain and noise distribution based upon the circuit 95 as illustrated schematically in FIG. 9. To relate the results of the following analysis to an actual SAW delay line 21, assume a SAW center frequency of 157 MHz and a SAW delay of 2.5 $\mu$S at the pulse detection threshold. Further assume the SAW delay line has an impulse response 98 that is an equilateral triangular pulse with a base width of 1.2 $\mu$S. This corresponds to a null-to-null bandwidth of 3.3 MHz. Since it is desired to minimize the temporal distortion, the measurement channel noise bandwidth will be set (rather arbitrarily) to 3 times the SAW null-to-null bandwidth, or 10 MHz by the bandpass filter 96 upstream from the envelope detector 97. Suppose that the desired measurement variance is 0.25 pS RMS and averaging $10^5$ iterations around the recirculating delay loop will be used, making the measurement interval 0.25 seconds. FIG. 9 shows a representative gain distribution assuming a recovery amplifier noise figure of 3 dB.

We can find the required peak signal to noise ratio from the desired measurement resolution. The relationship between the averaged and single event jitter is given by the following:

$$\tau_n = \text{variance} \times \sqrt{\text{No. measurement averages}} \quad (2)$$

$$0.25 \text{ pS RMS} \times \sqrt{10^5} = 80 \text{ pS RMS}$$

The noise level that caused this jitter is related to the detected waveform slew rate in the following manner:

$$e_n = \tau_n \times dv/dt \quad (3)$$

$$80 \text{ pS RMS} \times \frac{8.5 \text{ volts}}{600_{nS}} = 1.12 \text{ mV RMS}$$

Relating the noise to the peak signal in the usual manner it is found that to achieve a desired resolution the peak signal power at the SAW sensor 21 output must be 77.6 dB above the noise referred to the sensor output, or, −23.4 dBm peak, which is 4.57 $\mu$W peak.

The output energy in the triangular pulse 98, in FIG. 12, is found from its peak power and the integration of the instantaneous power, a squared function of time, over half the triangle pulse interval. Since this pulse is time symmetrical, the required SAW output energy is found to be:

$$J = 2 \times \int_0^{t/2} t^2 dt \quad (4)$$

$$\frac{2}{3} \times 600 \text{ nS} \times 4.57 \mu\text{W} = 1.83 \times 10^{-12} \text{ watt-sec}$$

The energy stored in the pulse generator capacitor 85 (FIG. 8B), or in the coaxial line 91 (FIG. 8C) is given by:

$$J = \frac{CE^2}{2} \text{ watt-sec} \quad (5)$$

For the sake of discussion, assume +V in FIG. 8B is 20 volts and the charged capacitor 85 is 30 pF. From this we find that the energy stored is $6 \times 10^{-9}$ watt-sec of which $3 \times 10^{-9}$ watt-sec is available to the load. Comparing this to the output energy required, from eq. 4, it is found that the maximum loss that can be accommodated is given by:

$$\text{Max.Loss} = 10\log \frac{1.83 \times 10^{-12}}{3 \times 10^{-9}} = -32 \text{ dB} \quad (6)$$

It is important to remember that this loss applies to all causes, including spectral loss, not just the CW insertion loss of the SAW delay line. However, it is also important to recall that the time displacement, time diversity matching, and randomization permit matching the SAW transducers for a substantial conjugate match, which is not usually the case in the interest of time spurious suppression.

Figure 10:
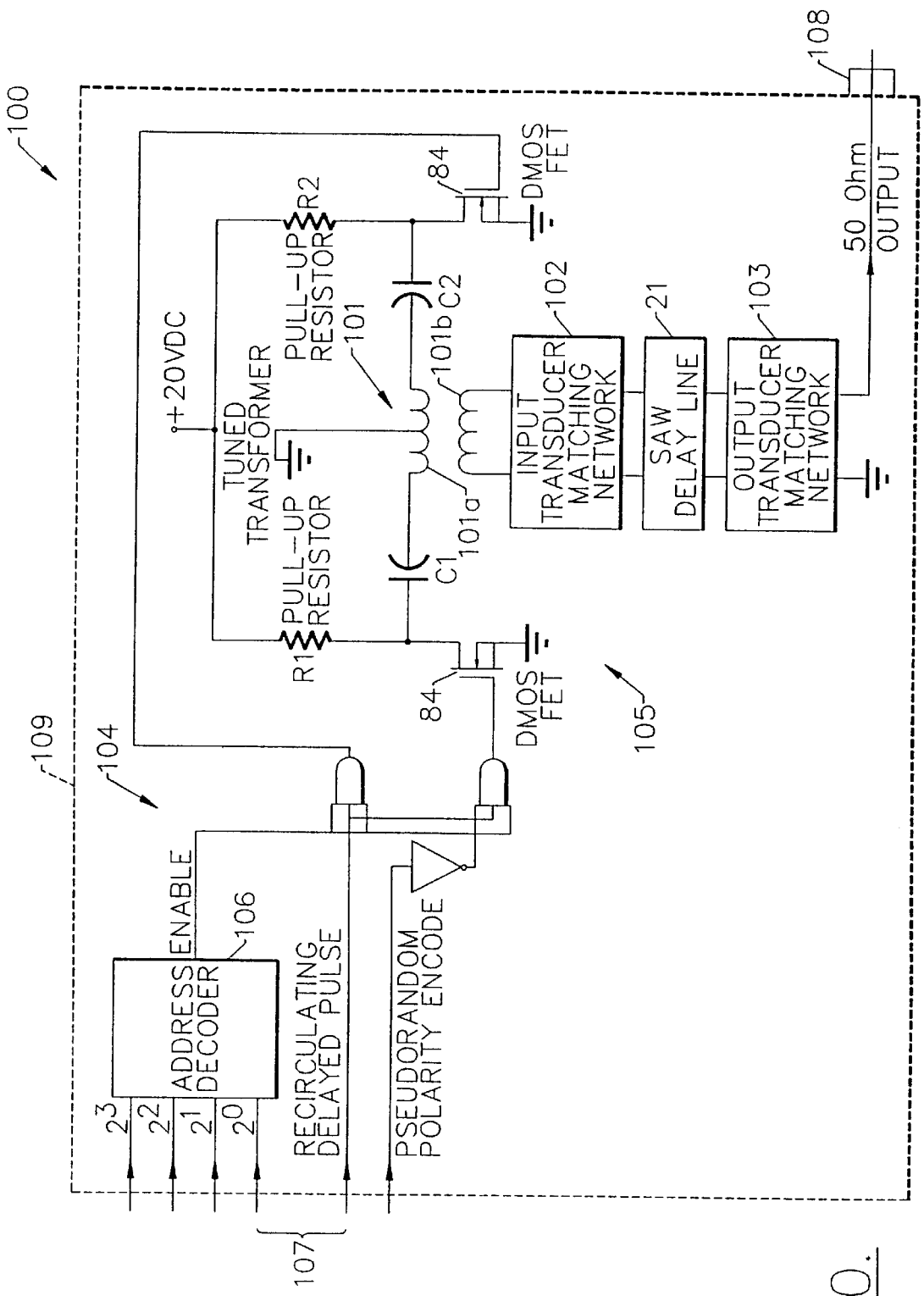
FIG. 10 is a schematic diagram of an integrated circuit differential driver and SAW sensor package in accordance with the present invention.

Referring now additionally to FIG. 10, a SAW delay package 100 suitable for use in an array and including a SAW delay device 21 and a differential driver 105 according to the invention is described. The 20 volt supply generator may be readily implemented with any of a number of inexpensive, low power, DC to DC converter chips which permit output voltage doubling, such as the Maxim MAX632 or MAX633 monolithic step-up switching regulators as would be readily understood by those skilled in the art.

Note that the circuit 105 is normally off, conserving power. An enable line is activated by a decoder 106 selecting the SAW sensor represented as the load to the tuned transformer 101. The output of the pseudorandom sequence generator 25 (FIG. 7) cooperates with the trigger means 104 thereby causing the discharge of either C1 or C2 through the tuned transformer. The direction of discharge current flow through the transformer primary 101a establishes the starting phase of the RF pulse as seen across the transformer secondary 101b.

The transformer secondary 101b can be imbedded in the SAW vapor sensor input matching network 102. Improved spectral efficiency may be realized by transitional coupling the circuit as a double-tuned transformer with a maximally flat transfer function. If this driver is configured using ACMOS gates, for example, the only notable power dissipated is in the pull-up resistors R1, R2 during discharge and recharge. Since the pulse discharge is completed in a fraction of the recirculating pulse interval, the power dissipated in the pull-up resistors R1, R2 is related to the duty cycle of the drive pulse which is typically in the order of 5%. The pull-up resistors can be rather large valued since the capacitors need not reach full charge until another recirculating pulse arrives.

The differential driver circuit 105 including the illustrated DMOS FETs 84 is readily amenable to thick-film integration and is simple enough to be integrated in the same package 100 as the SAW sensor 21 and output matching network 103. This is highly desirable since the sensor input interface is digital and the output interface 103 can be a convenient coaxial cable impedance in the range of about 25 to 100 ohms, such as 50 ohms, making it very easy to fabricate the illustrated sensor as a plug-in assembly having a housing 109 and associated connecting pins 107 and a coaxial connector 108 to thereby be much less susceptible to variations in parasitics than prior art devices. As would be readily understood by those skilled in the art, other connector arrangements are also contemplated by the present invention. As would also be readily understood by those skilled in the art, the SAW sensor 21 may include one or more pairs of interdigitated electrodes on a piezoelectric layer, in turn, positioned within the package 100.

In a prior art oscillator array, a plug-in sensor assembly would be impractical since the sensor is often used at a much higher oscillator circuit impedance level. Since the different polymers are used to coat the SAW sensors for different chemical species, the plug-in package makes the sensor measurement equipment field configurable, which is highly desirable.

Figure 11:
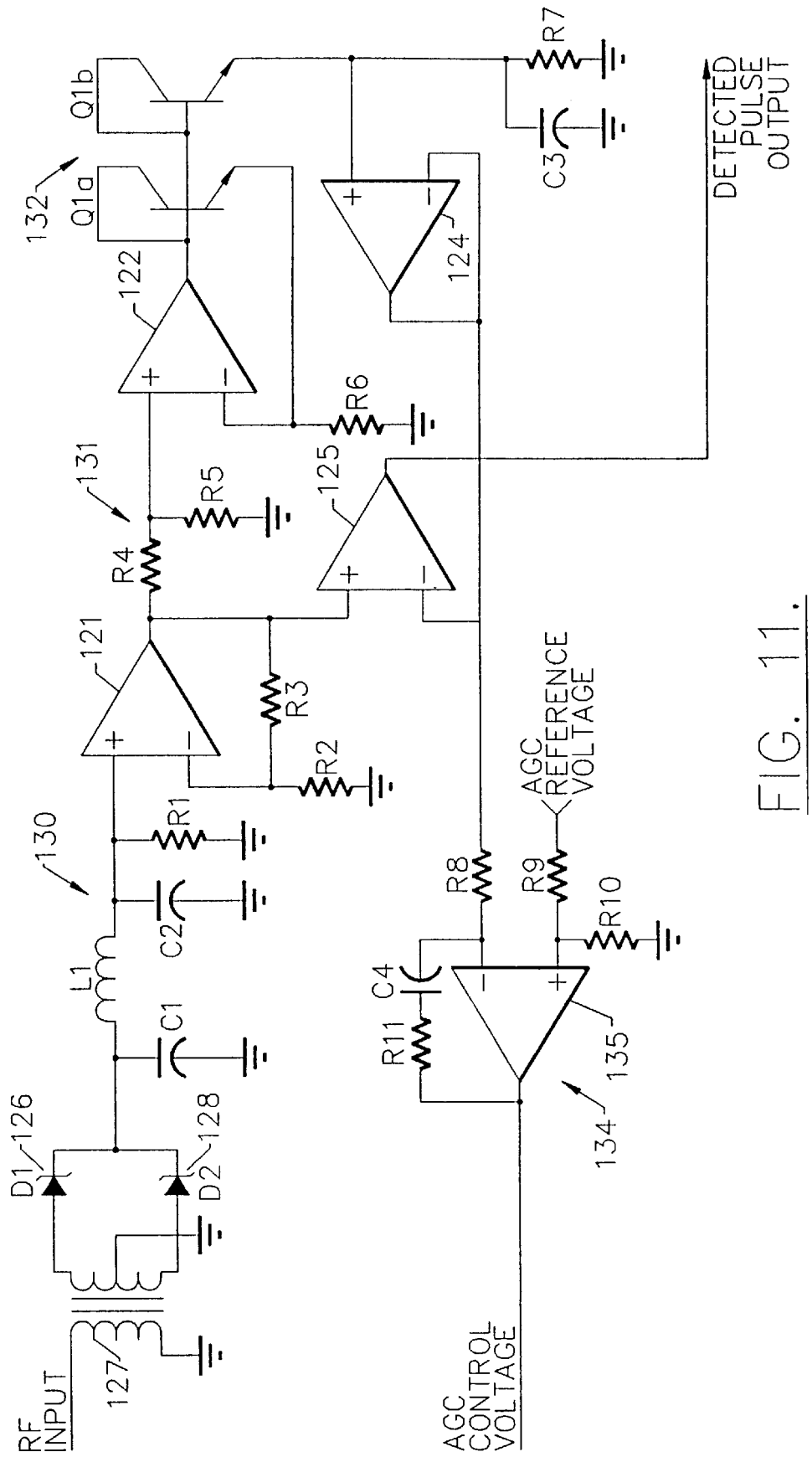
FIG. 11 is a schematic diagram of a ratiometric pulse detector for use in an embodiment of the apparatus in accordance with the present invention.

Turning now, additionally, to the schematic diagram of FIG. 11, a highly stable means of pulse detection is described. In this case, both the peak signal and noise levels indicated in FIG. 9 are reduced somewhat by gain scaling to levels appropriate for use with the circuit in FIG. 11. Typically, this results in a pulse amplitude of 2.5 volts peak at the output amplifier 121.

R.F. pulses from the low noise amplifier (LNA) 57 are presented to the full wave envelope detector comprised of transformer 127, and diodes 126 and 128. A low pass filter 130, comprised of C1, L1, C2 and Ri, is used to remove carrier ripple from the detected pulse amplitude. The output of amplifier 121 is presented to the positive input terminal of differential comparator 125 whose threshold is established by the voltage appearing at its negative input terminal. The comparator 125 is a high speed comparator, such as a MAXIM 913.

A fraction of the pulse amplitude appearing at the input to the comparator 125 is established by the voltage divider 131 comprised of R4 and R5.

A precision peak detector, comprised of the circuitry associated with amplifiers 122 and 124 generates a voltage which is proportional to a fraction of the peak pulse amplitude appearing at the positive input to the comparator 125.

The peak detector is rendered largely immune to ambient temperatures variations by using a precision matched monolithic transistor pair 132 such as the Analog Devices MAT-01, as matched diodes, represented by $Q1_a$ and $Q1_b$. This is feasible since the peak pulse amplitude is scaled to be less than the emitter-base breakdown voltage of $Q1_b$, which is in the order of 5 volts.

The peak voltage appearing at the positive input to amplifier 124 is stored in C3. Since the pulses are repetitious, the voltage of C3 need not reach its final value with a single pulse, thus relieving the drive requirements of amplifier 122 and $Q1_a$.

The resistor, R7, is used to provide a bleed for the input bias current of buffer 124. The time constant formed by R7 and C3 is chosen to be very long with respect to the recirculating pulse PRF, thus obviating any significant ripple on the stored peak amplitude.

The voltage appearing at the output of amplifier 124 is used both for the threshold of comparator 125 and as an error signal for an integrating automatic gain control loop 134 provided by amplifier 135 and its associated circuitry.

Temperature compensation for frequency variable circuits, such as the SAW matching circuits, and the low pass filter represented by C1, L1, and C2, can be comprehended directly or through the use of the temperature sensing diodes associated with the envelope detector diodes, D1 and D2. A compensating signal can be derived from the temperature sensing diodes and used to inject a small current at the junction of R4, R5, and amplifier 122. From the foregoing, it should be clear that the pulse/level detection process, itself, need not limit measurement resolution, as compared to the effects of finite signal to noise ratio, previously discussed.

Other features and advantages of the present invention may be gathered from copending, commonly assigned, patent applications entitled: "TIME DOMAIN DELAY DEVICE MEASUREMENT APPARATUS AND ASSOCIATED METHOD INCLUDING SENSOR PACKAGE" having Ser. No. 08/563,521, "TIME DOMAIN DELAY DEVICE MEASUREMENT APPARATUS AND ASSOCIATED METHOD" having Ser. No. 08/563,393, and "DIFFERENTIAL PHASE VELOCITY DETERMINING DELAY MEASUREMENT APPARATUS AND ASSOCIATED METHOD" having Ser. No. 08/563,397 the entire disclosures of each of which are incorporated herein in their entirety by reference.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A sensing apparatus for generating an output signal related to at least one sensed quantity, said sensing apparatus comprising:

at least one ultrasonic delay sensor having a delay related to the sensed quantity;

pulse recirculating means operatively connected to said at least one ultrasonic delay sensor for recirculating pulses therethrough; and measurement difference output means for generating said output signal related to the sensed quantity based upon a difference between first and second pulse time delay measurements for pulses recirculating through said at least one ultrasonic delay sensor, wherein said measurements difference output means comprises up-down counter means for counting pulses during the first measurement in one direction and for counting pulses during the second measurements in an opposite direction so that remaining counter contents represent a difference in delay between the first and second measurements.

2. A sensing apparatus according to claim 1 further comprising a reference ultrasonic delay device; and wherein said measurement difference output means includes means for generating the output signal based upon a difference between first and second measurements of said at least one ultrasonic delay sensor and said reference ultrasonic delay device, respectively.

3. A sensing apparatus according to claim 2 wherein said measurement difference output means comprises up-down counter means for counting pulses during the first measurement in one direction and for counting pulses during the second measurement in an opposite direction so that remaining counter contents represent a difference in delay between said at least one ultrasonic delay sensor and said reference ultrasonic delay device, respectively.

4. A sensing apparatus according to claim 1 wherein said pulse recirculating means comprises:

pulse generator means for generating a series of input pulses to said at least one ultrasonic delay sensor; and pulse detector means for detecting a series of output pulses after propagation through said at least one ultrasonic delay sensor.

5. A sensing apparatus according to claim 4 wherein said at least one ultrasonic delay sensor generates undesired multiple reflections from pulses propagating therethrough; and further comprising reflection suppression means for suppressing effects of the undesirable reflections generated by said at least one ultrasonic delay sensor.

6. A sensing apparatus according to claim 5 wherein said reflection suppression means further comprises random phase switching means cooperating with said pulse generator means for randomly switching phases of the series of input pulses to said at least one ultrasonic delay sensor to thereby reduce effects of the undesired reflections.

7. A sensing apparatus according to claim 5 wherein said reflection suppression means further comprises a fixed delay operatively connected between said pulse detector means and said pulse generator means to thereby reduce effects of the undesired reflections.

8. A sensing apparatus according to claim 5 wherein said reflection suppression means further comprises time diversity matching means operatively connected between said pulse generator means and said at least one ultrasonic delay sensor for providing a conjugate match therebetween during a time interval of each pulse and providing a relatively large mismatch at other times.

9. A sensing apparatus according to claim 1 wherein said pulse recirculating means further comprises time base means for generating a time base signal having a predetermined time base period.

10. A sensing apparatus according to claim 1 wherein said at least one ultrasonic delay sensor comprises a plurality of ultrasonic delay sensors; and further comprising time division multiplex means for successively connecting said pulse recirculating means to each of the plurality of ultrasonic delay sensors to generate a plurality of output signals related to corresponding sensed quantities.

11. A sensing apparatus according to claim 1 wherein said at least one ultrasonic delay sensor is at least one surface acoustic wave (SAW) vapor sensor; and wherein said measurement difference output means further comprises vapor concentration output means for generating the output signal related to vapor concentration sensed by said at least one SAW vapor sensor.

12. A sensing apparatus according to claim 1 wherein said at least one ultrasonic delay sensor is at least one ultrasonic delay particulate sensor, and wherein said measurement difference output means further comprises particulate output means for generating the output signal related to a particulate sensed by said at least one ultrasonic delay particulate sensor.

13. A sensing apparatus according to claim 1 wherein said at least one ultrasonic delay sensor is at least one ultrasonic delay pressure sensor, and wherein said measurement difference output means further comprises pressure output means for generating the output signal related to pressure sensed by said at least one ultrasonic delay pressure sensor.

14. An apparatus for generating an output signal related to delay of a plurality of ultrasonic delay devices, said apparatus comprising:

pulse recirculating means for recirculating pulses through the plurality of ultrasonic delay devices; and measurement difference output means for generating said output signal based upon a difference between first and second pulse time delay measurements for pulses recirculating through the plurality of ultrasonic delay devices, said measurement difference output means comprising up-down counter means for counting pulses during the first measurement in one direction and for counting pulses during the second measurement in an opposition opposite direction so that remaining counter contents represent a difference in delay between the first and second measurements said measurement difference output means further including means for generating the output signal based upon a difference between first and second measurements of first and second delay devices, respectively.

15. An apparatus according to claim 14 wherein said pulse recirculating means comprises:

pulse generator means for generating a series of input pulses to the at least one ultrasonic delay device; and pulse detector means for detecting a series of output pulses after propagation through the at least one ultrasonic delay device.

16. An apparatus according to claim 15 wherein the ultrasonic delay device generates undesired multiple reflections from pulses propagating therethrough; and further comprising reflection suppression means for suppressing effects of the undesirable reflections generated by the ultrasonic delay device.

17. An apparatus according to claim 16 wherein said reflection suppression means further comprises random phase switching means cooperating with said pulse generator means for randomly switching phases of the series of input pulses to the at least one ultrasonic delay device to thereby reduce effects of the undesired reflections.

18. A sensing apparatus according to claim 16 wherein said reflection suppression means further comprises a fixed delay operatively connected between said pulse detector means and said pulse generator means to thereby reduce effects of the undesired reflections.

19. An apparatus according to claim 16 wherein said reflection suppression means further comprises time diversity matching means operatively connected between said pulse generator means and the at least one ultrasonic delay device for providing a conjugate match therebetween during a time interval of each pulse and providing a relatively large mismatch at other times.

20. An apparatus according to claim 14 wherein said pulse recirculating means further comprises time base means for generating a time base signal having a predetermined time base period.

21. An apparatus according to claim 14 wherein the at least one ultrasonic delay device comprises a plurality of ultrasonic delay devices; and further comprising time division multiplex means for successively connecting said pulse recirculating means to each of the plurality of ultrasonic delay devices to generate a plurality of output signals.

22. An apparatus according to claim 14 wherein the at least one ultrasonic delay device is at least one surface acoustic wave (SAW) vapor sensor; and wherein said measurement difference output means further comprises vapor concentration output means for generating the output signal related to vapor concentration sensed by the at least one SAW vapor sensor.

23. A sensing apparatus according to claim 14 wherein said at least one ultrasonic delay sensor is at least one ultrasonic delay particulate sensor, and wherein said measurement difference output means further comprises particulate output means for generating the output signal related to a particulate sensed by said at least one ultrasonic delay particulate sensor.

24. An apparatus according to claim 14 wherein the at least one ultrasonic delay device is at least one ultrasonic delay pressure sensor, and wherein said measurement difference output means further comprises pressure output means for generating the output signal related to pressure sensed by the at least one ultrasonic delay pressure sensor.

25. A method for generating an output signal related to delay of at least one ultrasonic delay device, said method comprising the steps of:

recirculating pulses through the at least one ultrasonic delay device;

counting pulses during a first measurement in one direction in up-down counter means;

counting pulses during a second measurement in an opposite direction in the up-down counter means so that remaining counter contents represent a difference in delay between the first and second measurements; and generating said output signal based upon the difference between the first and second pulse time delay measurements for pulses recirculating through the at least one ultrasonic delay device.

26. A method according to claim 25 wherein the at least one ultrasonic delay device comprises a reference ultrasonic delay device; and wherein the step of generating the output signal comprises the step of generating the output signal based upon a difference between first and second measurements of an ultrasonic delay device and the reference ultrasonic delay device, respectively.

27. A method according to claim 25 wherein the step of recirculating pulses comprises the steps of:
generating a series of input pulses to the at least one ultrasonic delay device; and
detecting a series of output pulses after propagation through the at least one ultrasonic delay device.

28. A method according to claim 27 wherein the at least one ultrasonic delay device generates undesired multiple reflections from pulses propagating therethrough, and further comprising the step of suppressing effects of the undesirable reflections generated by the at least one ultrasonic delay device.

29. A method according to claim 28 wherein the step of suppressing reflections comprises the step of randomly switching phases of the series of input pulses to the at least one ultrasonic delay device to thereby reduce effects of the undesired reflections.

30. A method according to claim 28 wherein the step of suppressing reflections comprises the step of operatively connecting a fixed delay in a feedback path for recirculating pulses through the at least one ultrasonic delay device to thereby reduce effects of the undesired reflections.

31. A method according to claim 28 wherein the step of suppressing reflections further comprises the step of providing a conjugate match between a pulse generator and the at least one ultrasonic delay device during a time interval of each pulse and providing a relatively large mismatch at other times.

32. A method according to claim 25 wherein the step of recirculating pulses further comprises the step of generating a time base signal having a predetermined time base period.

33. A method according to claim 25 wherein the at least one ultrasonic delay device comprises a plurality of ultrasonic delay devices; and further comprising the steps of successively recirculating pulses through each of the plurality of ultrasonic delay devices and generating a plurality of output signals.

34. A method according to claim 25 wherein the at least one ultrasonic delay device is at least one surface acoustic wave (SAW) vapor sensor; and wherein the step of generating the output signal further comprises the step of generating the output signal related to vapor concentration sensed by the at least one SAW vapor sensor.

35. A method according to claim 25 wherein the at least one ultrasonic delay device is at least one ultrasonic delay particulate sensor; and wherein the step of generating the output signal further comprises the step of generating the output signal related to a particulate sensed by the at least one ultrasonic delay particulate sensor.

36. A sensing apparatus for generating an output signal related to at least one sensed quantity, said sensing apparatus comprising:
a plurality of ultrasonic delay sensors, each having a delay related to the sensed quantity;
pulse recirculating means operatively connected to said at least one ultrasonic delay sensor for recirculating pulses therethrough; and
measurement difference output means for generating said output signal based upon a difference between first and second pulse time delay measurements of first and second ultrasonic delay sensors.

37. A sensing apparatus according to claim 36 wherein said measurement difference output means comprises up-down counter means for counting pulses during the first measurement in one direction and for counting pulses during the second measurement in an opposite direction so that remaining counter contents represent a difference in delay between the first and second measurements of said first and second ultrasonic delay sensors, respectively.

38. An apparatus for generating an output signal related to delay of at least one ultrasonic delay device, said apparatus comprising:
pulse recirculating means for recirculating pulses through the at least one ultrasonic delay device; and
measurement difference output means for generating said output signal based upon a difference between first and second pulse time delay measurements for pulses recirculating through the at least one ultrasonic delay device, said measurement difference output means comprising up-down counter means for counting pulses during the first measurement in one direction and for counting pulses during the second measurement in an opposite direction so that remaining counter contents represent a difference in delay between the first and second measurements, wherein one of the at least one ultrasonic delay device further comprises a reference ultrasonic delay device, and wherein said measurement difference output means includes means for generating the output signal based upon a difference between first and second measurements of an ultrasonic delay device and the reference ultrasonic delay device, respectively.

39. A method for generating an output signal related to delay of a plurality of ultrasonic delay devices, said method comprising the steps of:
recirculating pulses through the plurality of ultrasonic delay devices; and
generating said output signal based upon a difference between first and second pulse time delay measurements of first and second ultrasonic delay devices, respectively.

* * * * *